United States Patent [19]

Ciavattoni et al.

[11] 4,247,779
[45] Jan. 27, 1981

[54] LINK-CLUTCH FILM DRIVE MECHANISM FOR PANORAMIC DENTAL X-RAY MACHINE

[75] Inventors: Anthony Ciavattoni, Staten Island, N.Y.; Jack Flynn, Monmouth; Josef Ujvary, Kingston, both of N.J.

[73] Assignee: Pennwalt Corporation, Philadelphia, Pa.

[21] Appl. No.: 25,127

[22] Filed: Mar. 29, 1979

[51] Int. Cl.³ .................................................. A61B 6/14
[52] U.S. Cl. ................................................. 250/439 P
[58] Field of Search ..................................... 250/439 P

[56] References Cited

U.S. PATENT DOCUMENTS

| | | | |
|---|---|---|---|
| 2,798,958 | 7/1957 | Hudson et al. | 250/439 P |
| 3,045,118 | 7/1962 | Hollman et al. | 250/439 P |
| 4,039,837 | 8/1977 | Ohta et al. | 250/439 P |
| 4,125,774 | 11/1978 | Ciavattoni et al. | 250/439 P |
| 4,172,977 | 10/1979 | Ciavattoni et al. | 250/439 P |

Primary Examiner—Alfred E. Smith
Assistant Examiner—T. N. Grigsby

[57] ABSTRACT

Film drive mechanism for use with a panoramic X-ray machine which provides continuous and discontinuous radiographic images of dental arch areas of a shifting patient. The mechanism utilizes electromagnetic clutches, linkage structures and cams for varying the rotational speed of a film drive shaft in accordance with the mode of radiographing selected, i.e., continuous or discontinuous. The film drive shaft controls rotation of a drum which has the film wrapped therearound.

12 Claims, 8 Drawing Figures

LINK-CLUTCH FILM DRIVE MECHANISM FOR PANORAMIC DENTAL X-RAY MACHINE

CROSS-REFERENCED TO OTHER RELATED PATENT APPLICATIONS

Reference is hereby made to Ser. No. 002,148, filed Jan. 9, 1979, for "Panoramic Dental X-Ray Machine X-Motion Drive" of R. Cushman et al., assigned to the assignee hereof.

STATEMENT OF THE INVENTION

The present invention relates to X-ray apparatus and more particularly concerns film drive mechanism which coordinates the speed of X-ray film travel with chair shift and transport to provide undistorted continuous and discontinuous radiographs of dental arch areas.

BACKGROUND OF THE INVENTION

Prior art panoramic dental X-ray apparatus are well known in the art. Some provide a continuous image of the dental arch area and commonly employ an X-ray source and X-ray film supported on a rotatable carrying arm which orbits a patient situated in the beam path. The patient may remain stationary in the chair, or the chair may be transported in accordance with various X-Y type drive mechanisms in order to simulate the generally elliptical shape of the human dental arch, as disclosed in U.S. Pat. No. 4,125,774, assigned to the present assignee. The continuous image radiograph provides the dentist with a panoramic view of the teeth and associated structures and is a useful diagnostic aid in many phases of dental practice.

Various other prior art apparatus provide a discontinuous, or split image panoramic radiograph which possesses certain advantages. Here, the dentist is provided with additional interpretive information since two distinctly different views of the incisors, or centrals area are provided. For example, in U.S. Pat. No. 3,045,118, apparatus is disclosed which automatically shifts the patient in order that the line of sight between the X-ray source and film bypasses the patient's spinal column and permits X-raying of the other half of the dental arch. Apparatus is also disclosed therein for continuously moving an X-ray source and extra-oral film holder about the patient.

In U.S. Pat. No. 2,798,958, means are disclosed for reorienting the patient after completion of one-half of the excursion cycle in order to relocate the center of the axis of rotation with respect to the patient's head prior to X-raying the other one-half of the dental arch in order to provide the discontinuous, or split radiographic images.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the chair shift or transport, and the rate of travel of the X-ray source about the patient's head in order that the radiological projections occupy a distance on the film equal to the linear distance of a curved structure being X-rayed, such as a typical dental arch.

The present invention discloses film drive mechanism which is readily adaptable for use with structure disclosed in cross-referenced patent application Ser. No. 002,148, for "Panoramic Dental X-Ray Machine X-Motion Drive," or with other suitable panoramic dental X-ray machines which provide either or both continuous and discontinuous radiographic images.

DETAILED DESCRIPTION OF THE INVENTION

Figure 1:
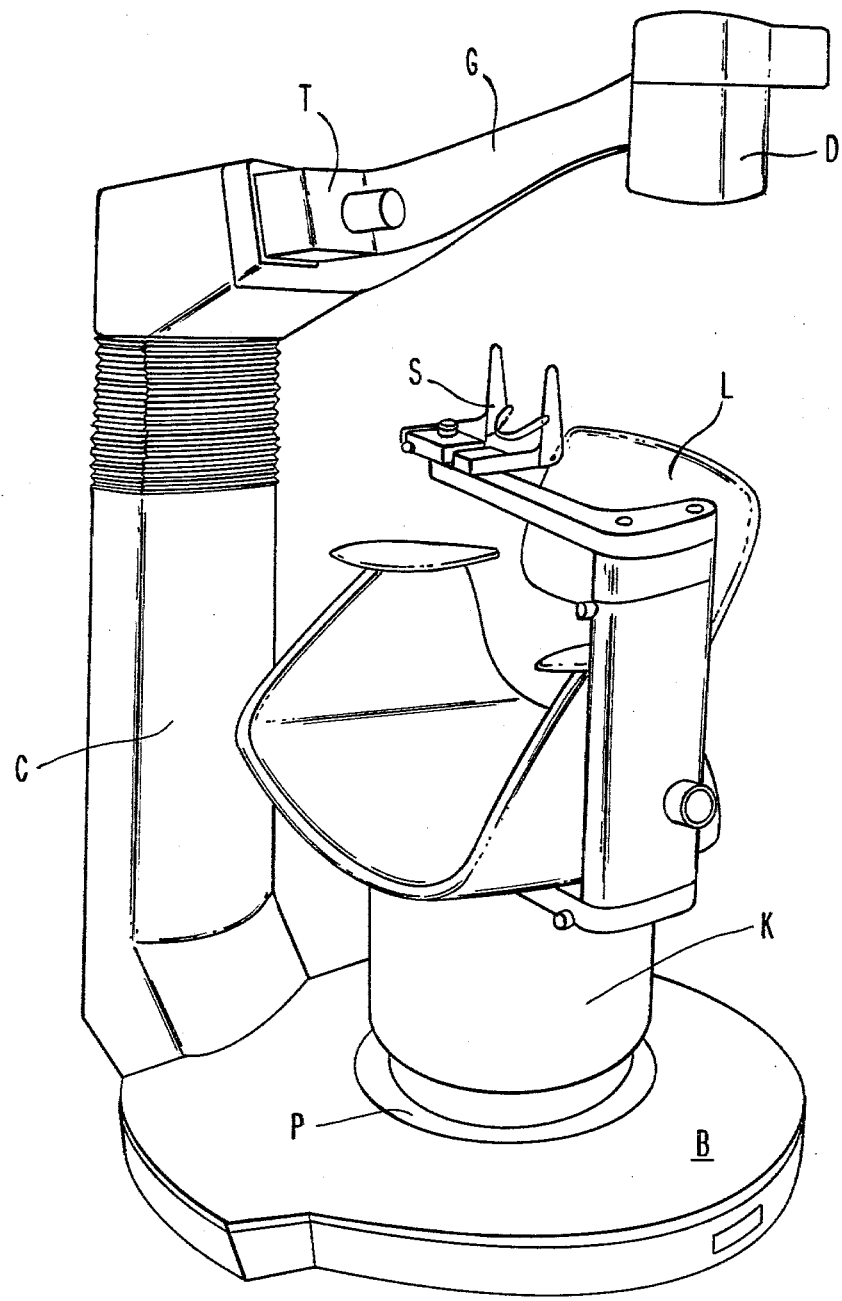
FIG. 1 is a perspective view of an assembled panoramic dental X-ray machine employing the film drive mechanism of the invention.
Figure 2:
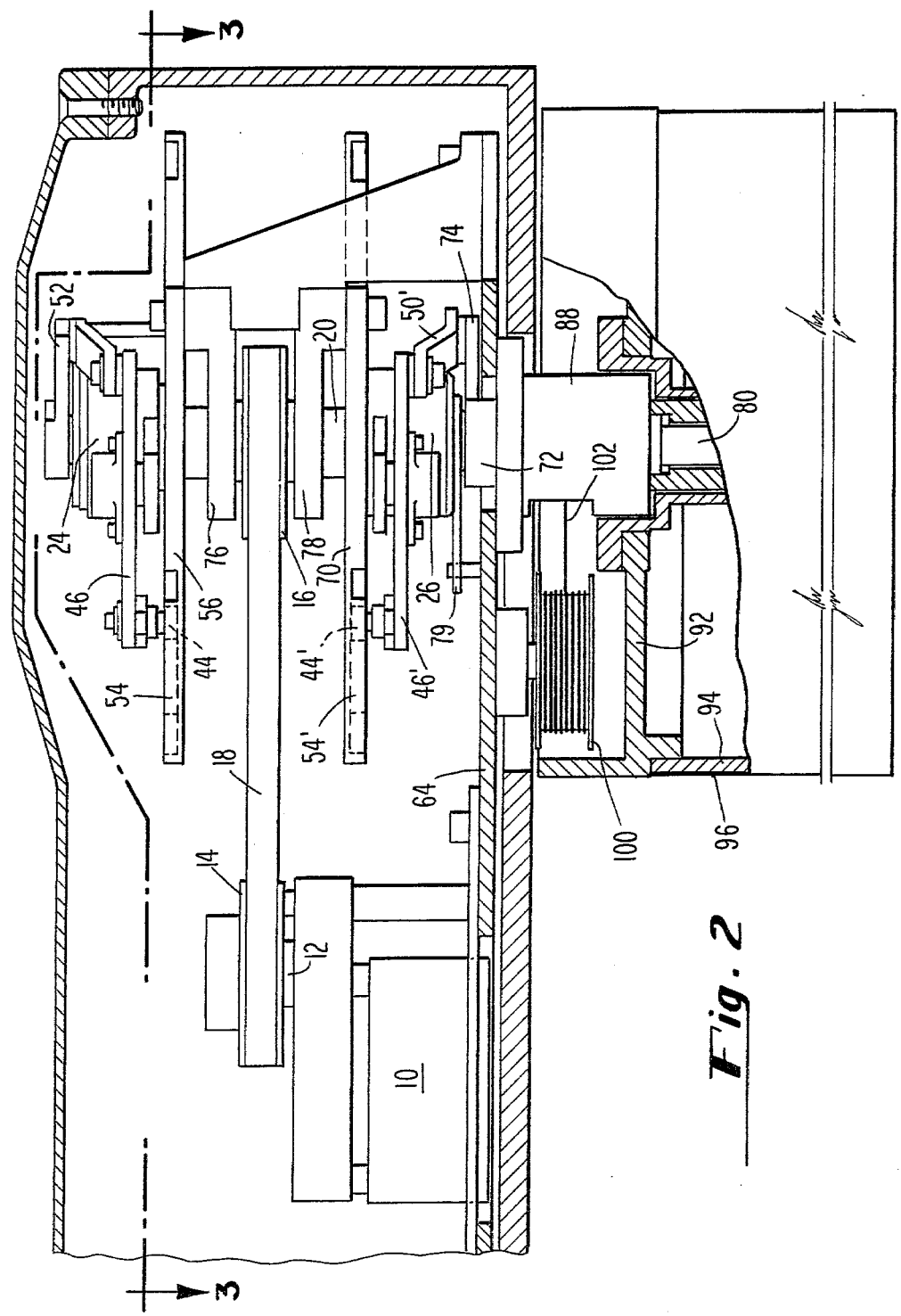
FIG. 2 is a diagrammatic elevational view, partially sectioned, of the film drive mechanism of the invention.
Figure 3:
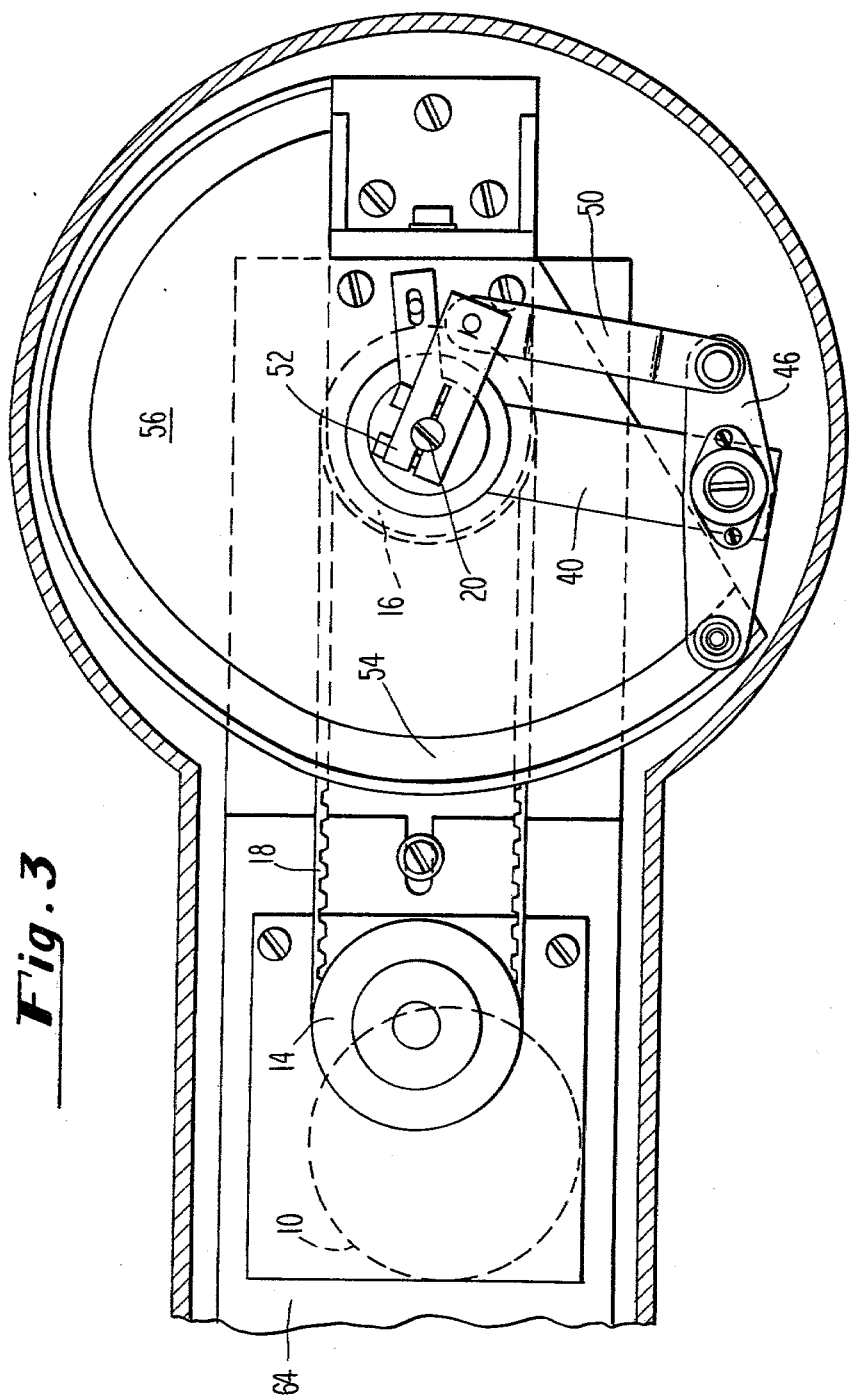
FIG. 3 is a view of the film drive mechanism of FIG. 2 looking in the direction of the arrows 3—3.

Referring to FIG. 1 of the drawings, the panoramic X-ray machine comprises a base B having a stationary platform P disposed generally centrally thereof. Platform P supports a patient chair L including means S for supporting the chin and head of a patient. A column C is caused to rotate around chair L, the column carrying a tubehead T, a camera supporting arm G, and a camera assembly D which houses the film drive mechanism of the present invention. The chair shift and transport mechanism is located below chair L, within shroud K, the mechanism being bolted securely to stationary platform P. The excursion mechanism for causing column C to rotate around stationary platform P at a uniform and constant rate is supported and partially housed in base B.

Referring to FIGS. 2, 3, 4 and 5, the film drive mechanism of the present invention is housed within camera assembly D and comprises a reversible, synchronous motor 10 having shaft 12 which slowly rotates pulley 16 through timing belt 18 connected therebetween. Pulley 16 rotates about an inner shaft 20. A pair of electromagnetic clutches 24 and 26 is positioned about inner shaft 20, clutch 24 being disposed above pulley 16 and clutch 26 being disposed therebelow. Clutches 24 and 26 are provided with armatures 28 and 30 respectively which armatures rotate with pulley 16. Either clutch may be separably energized through its permanent magnet M. Energization of upper clutch 24, for example, magnetically couples the rotating armature 28 to rotor 32, slidably rotatable around inner shaft 20 by means of a bushing 34, suitably plastic, which bushing also lends dimensional stability to rotor 32.

Figure 4:
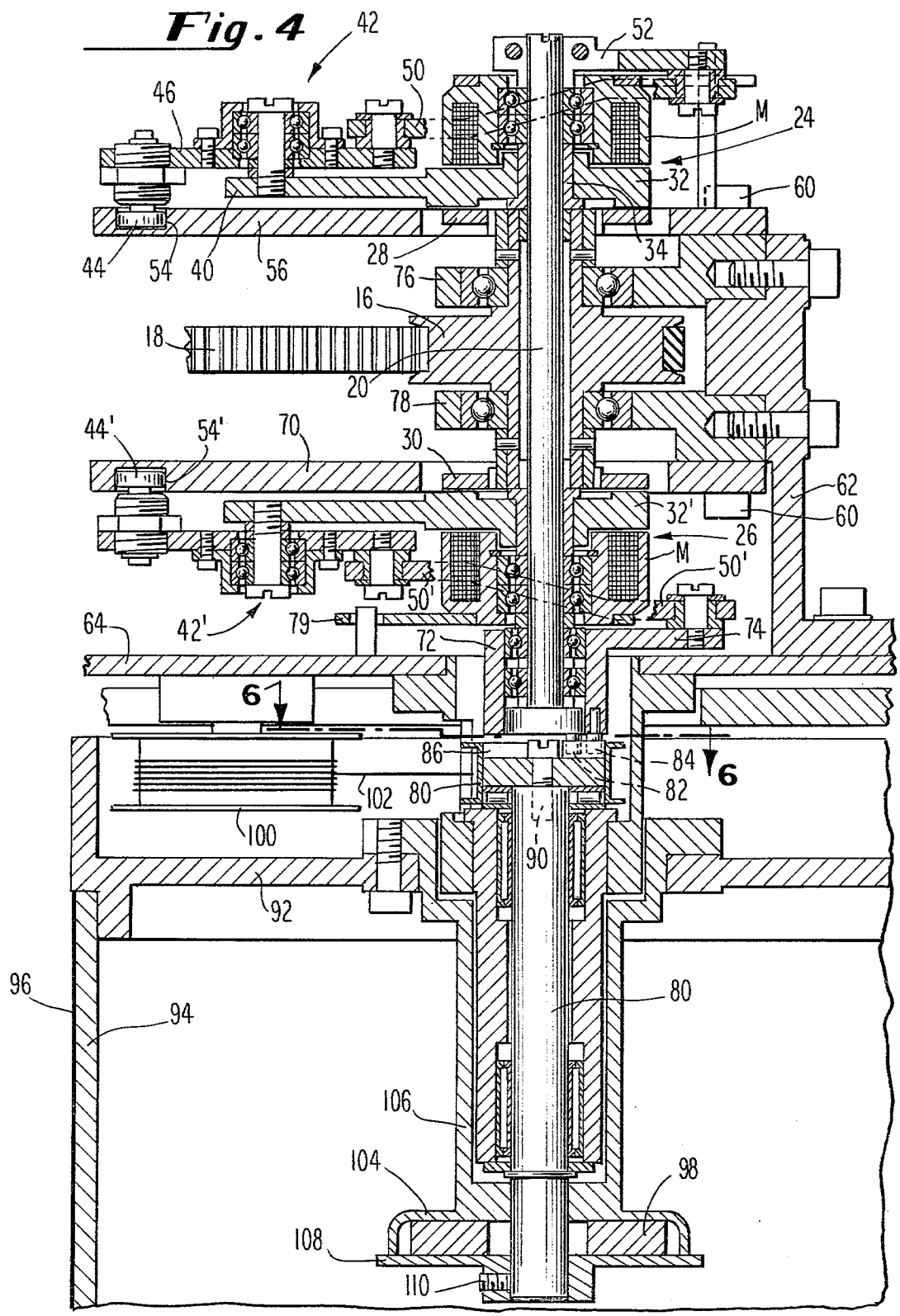
FIG. 4 is a longitudinal sectional view of the film drive mechanism, parts omitted for clarity.
Figure 5:
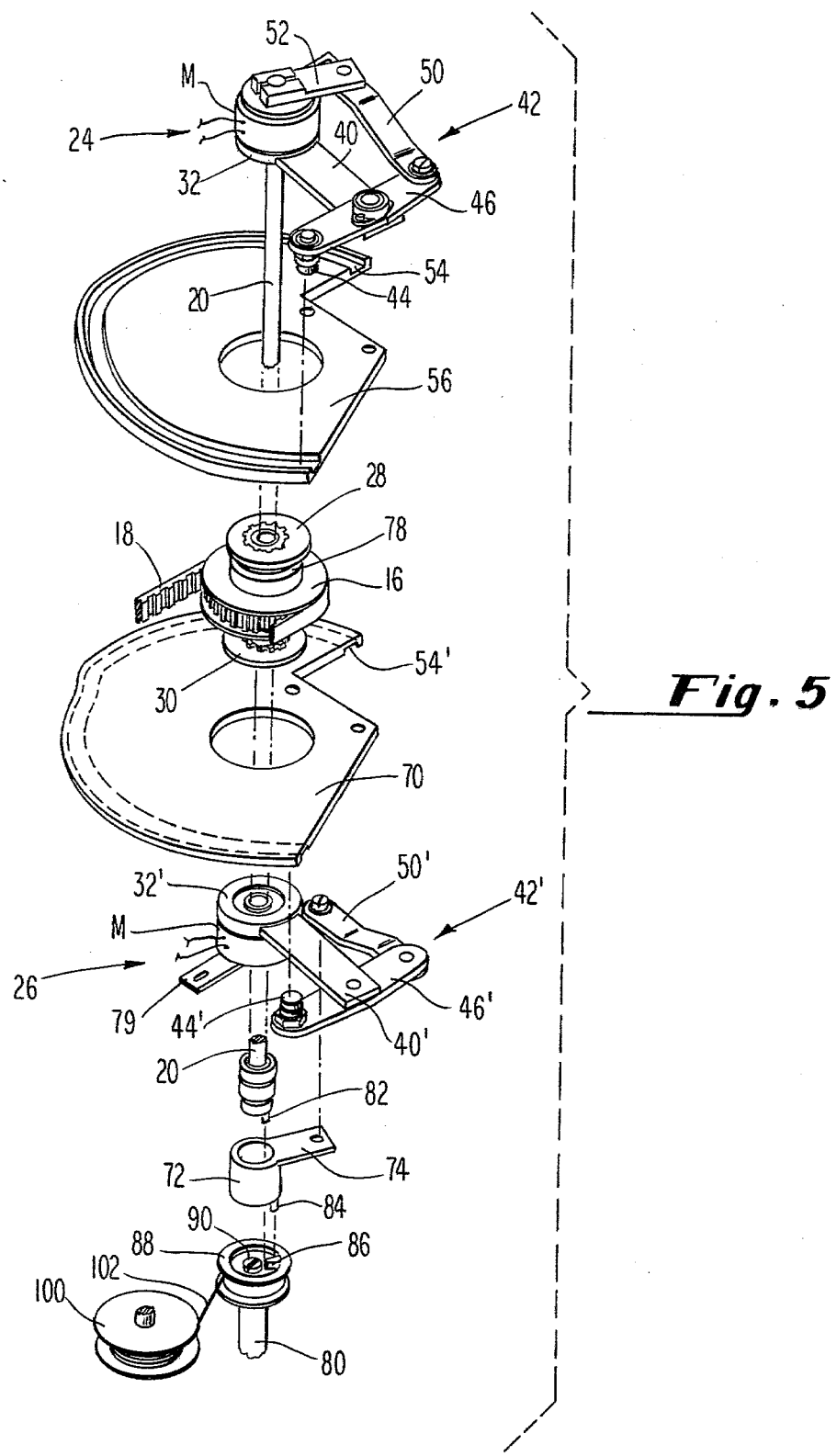
FIG. 5 is an exploded perspective view of the film drive mechanism employed in the machine of FIG. 1.

Rotor 32 is connected to one end of a link arm 40 as shown in FIG. 5, or they may be integrally formed as in FIG. 4. Rotation of rotor 32 rotates link arm 40. The other end of link arm 40 is pivotally connected to an upper linkage arrangement 42 which includes a cam follower 44 mounted on one end of lever arm 46 which is pivotally connected at a central portion thereof to link arm 40. A connecting link 50 pivotally interconnects a crank 52 which is secured to an upper portion of inner shaft 20, and the other end of lever arm 46. Cam follower 44 rides in a groove 54 disposed in an upper surface of a cam member 56 used in providing the continuous radiographic images. Thus, the rate of rotational movement of inner shaft 20 is controlled by linkage arrangement 42 cooperating with movement of cam follower 44 in groove 54.

"Continuous" cam 56 does not rotate. It is adjustably secured by locking pins 60 engaging vertical frame member 62 supported on horizontal plate support member 64 which also supports motor 10. Approximately 250° of rotation of inner shaft 20 by crank 52 is needed in order to drive the film drive shaft, later described, for a complete continuous radiograph.

Another cam member 70 is provided below pulley 16 when discontinuous or split radiographic images are desired. Thus, a lower linkage arrangement 42', similar to upper linkage arrangement 42 is provide for effecting rotation of an outer shaft 72 concentrically disposed about a lower portion of inner shaft 20. Outer shaft 72 however is provided with a laterally extending arm 74 to which connecting link 50' is pivotally connected. Energization of lower electromagnetic clutch 26 causes armature 30 to magnetically couple rotor 32' which causes link arm 40', through lever arm 46' and connecting link 50', to urge cam follower 44' of lower linkage arrangement 42' to ride in groove 54' disposed in a bottom surface of "split" cam 70 to cause rotation of outer shaft 72. Inner shaft 20, of course, remains motionless during rotation of the outer shaft. Locking pins 60 prevent split cam 70 from rotating and also maintain bearing support members 76 and 78 in position between pulley 16 and clutches 24 and 26 respectively. Permanent magnet M is provided with an arm 79 which is secured to horizontal plate support 64 by screw means to prevent rotation of permanent magnet M.

Linkage arrangements 42 and 42', in cooperation with the cam follower-groove arrangements, are capable of advancing or retarding the speed of rotation of their respective shafts, i.e., inner shaft 20 or outer shaft 72, and hence, the speed of rotation of the film drive shaft, later described. The rate of changes of the distance of groove 54 from the inner shaft 20 as the follower 44 rides in the groove determines the rate of change of speed of rotation of the inner shaft and hence the film drive shaft. If the increase in distance is sharp, the inner shaft rotational speed increases sharply. If the distance decreases gradually, the shaft rotational speed decreases gradually. In the case of split or discontinuous images, distance of groove 54' from outer shaft 72 will control outer shaft speeds, and hence, film drive speeds. To further clarify, if a cam follower rode in a groove which coincided with a circle having its center at the center of the inner or outer shafts, the speed of rotation of the inner or outer shafts, and hence, the film drive shaft, would be constant.

In panoramic dental X-ray machines of the assignee, film travel speed is slower when the cuspid-incisor area is radiographed as compared to the posterior regions of the mouth. Groove configuration to provide desired film travel speeds at various portions of a typical dental arch structure may be calculated by a skilled mathematician and are not described herein.

The film drive shaft is designated 80 in the drawings. Pins 82 and 84 project downwardly from the periphery of the lowermost portions of inner and outer shafts 20 and 72 respectively. Rotation of either the inner or outer shafts causes its respective pin to abut against a fixed protrusion or boss 86 positioned within spool 88 which is fixedly axially secured to film drive shaft 80 at its upper end by means of screw 90. Thus, rotary motion of either pin causes rotation of film drive shaft 80 which accordingly rotates a drum holder disc 92. Secured to drum holder disc 92 is a drum 94 having X-ray film 96 wrapped therearound. It is apparent therefore that rate and speed of travel of film 96 is governed by rotation of the inner and outer shafts.

In order to align the starting position of drum 94 and X-ray film 96, a magnetic slip clutch 98, suitably in the form of an annulus or separate pieces, is secured to flanged portion 104 by pinning (not shown) or other convenient means. Plate 108 is removably affixed to film drive shaft 80 by screw 110. Alignment of the drum and film is achieved manually by rotating drum 94 to overcome the friction and attraction of magnetic slip clutch 98 to plate 108.

A tensioning spring pulley 100 is mounted to horizontal plate support 64 for rotation therebelow and within drum holder disc 92. Cable 102 is wound onto tension spring pulley 100 and take-up spool 88. In the forward, or radiographing mode, tension increases within tension spring pulley 100 to provide constant contact between boss 86 and either pin 82 or pin 84, depending on the mode of radiographing, i.e., continuous or discontinuous, thus insuring rotation of film drive shaft 80 in accordance therewith. Reversing the direction of rotation of shaft 12 of motor 10 will return cam follower 44 or 44' to its original or starting position upon energizing electromagnetic clutch 24 or 26 respectively.

Figure 6:
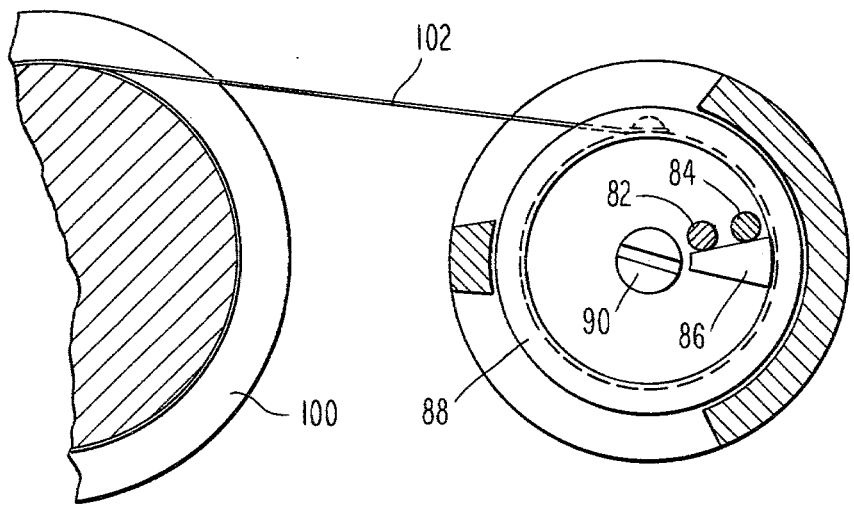
FIG. 6 is a partially sectioned view of the film drive mechanism of FIG. 4 looking in the direction of the arrows 6—6, illustrating an at-rest position.
Figure 7:
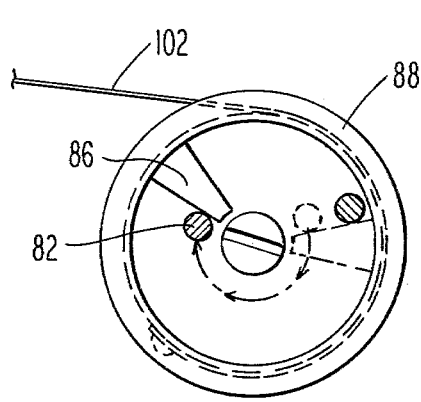
FIGS. 7 and 8 are views similar to FIG. 6 illustrating operating modes of the present film drive mechanism.
Figure 8:
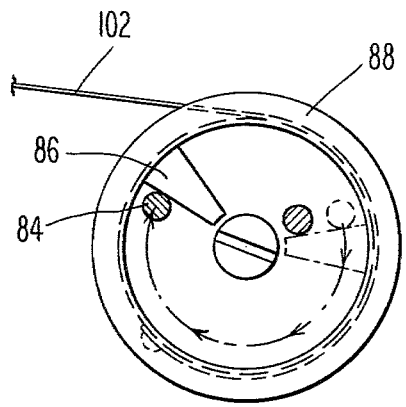

Referring now to FIG. 6, pins 82 and 84 are illustrated in their at-rest position. Tension spring pulley 100 exerts tension on cable 102 to thereby urge boss 86 of take-up spool 88 against the pins. Upon rotation of inner shaft 20, pin 82, depending therefrom, causes boss 86 to rotate in a clockwise direction (FIG. 7), and hence film drive shaft 80 mounted thereto by screw 90. In FIG. 8, pin 84 urges boss or protrusion 86 to rotate as shown. Pin 84 is connected to outer shaft 72 which is associated with radiographic images of the discontinuous type, whereas pin 82 comes into play when continuous type images are desired.

We claim:

1. In a panoramic dental X-ray machine for providing continuous and discontinuous radiographic images of dental arch areas of a patient seated in a chair which travels during at least a portion of said continuous and discontinuous modes of radiographing, said X-ray machine comprising
   (a) a tubehead containing an X-ray source and means to power said source,
   (b) a camera assembly comprising a rotating drum including X-ray film disposed therearound for activation by said X-ray source, said tubehead and said camera assembly rotating as a unit about said patient, the combination therewith of the improvement comprising
      film drive means mounted within said camera assembly for rotating said drum and film at controlled rates of drive in accordance with travel of said chair and selected mode of radiographing while said tubehead and camera assembly circularly orbit said patient, said film drive means comprising
      a pair of stationary cams, one of said cams having a groove disposed therein for providing said continuous image and other of said cams having another groove disposed therein for providing said discontinuous image, a pair of linking arrangements, each including a cam follower for riding in respective groove of respective cam, means for separably rotating each of said pair of linking arrangements and cam follower associated therewith, independently rotatable shaft means rotating in accordance with rotation of each of said pair of linking arrangements, a film drive shaft in operable alignment with said shaft means and responsive to rotation thereof whereby means for holding said X-ray film rotates in accordance with rotation of said film drive shaft to thereby rotate said film.

2. The machine of claim 1 wherein said pair of stationary cams are spaced plate cams.

3. The machine of claim 2 wherein said grooves for providing said continuous and discontinuous images are disposed in opposing surfaces of said plate cams.

4. The machine of claim 1 wherein said independently rotatable shaft means comprises an inner shaft and an outer shaft spaced concentrically from each other and having their lowermost portions in substantially coplanar relationship, said outer shaft being shorter in length than said inner shaft.

5. The machine of claim 4 further characterized by a pulley disposed about said inner shaft, means for rotating said pulley, a pair of clutches disposed about said inner shaft, each of said clutches cooperating with one each of said linking arrangements, each of said clutches having an armature disposed in spaced relationship about said inner shaft and rotating in accordance with said rotating pulley, means for separably magnetically coupling said rotating armature with a corresponding rotor member of said clutch, the rotating rotor member being slidably mounted about said inner shaft whereby that linking arrangement associated with said rotating rotor rotates in accordance therewith.

6. The machine of claim 5 wherein one of said pair of linking arrangements rotates said inner shaft and the other of said pair rotates said outer shaft.

7. The machine of claim 6 wherein a crank member has one of its ends fixedly secured to said inner shaft and other end pivotally connected to one end of a lever arm having its other end pivotally connected to said linking arrangement.

8. The machine of claim 6 wherein said outer shaft is provided with an arm extending laterally therefrom, said arm being pivotally connected to a linking member of that linking arrangement of said pair of linking arrangements associated with said outer shaft.

9. The machine of claim 6 wherein a pin depends from each of said lowermost portion of said inner shaft and said outer shaft, a spool axially aligned with said film drive shaft and secured to an uppermost portion thereof, a boss disposed within said spool, said pins separably contacting said boss to rotate said film drive shaft in accordance with rotation of that shaft from which said pin depends.

10. The machine of claim 9 wherein a tension spring pulley is rotatably mounted adjacent said spool for continuously urging said boss against said pin depending from said inner shaft for providing continuous radiographic images and against said pin depending from said outer shaft for providing discontinuous radiographic images.

11. The machine of claim 10 wherein a drum is mounted for rotation with said film drive shaft and said X-ray film is wrapped around said drum.

12. The machine of claim 11 wherein magnetic means is disposed within said drum adjacent a lower portion of said film drive shaft for permitting alignment of said drum and X-ray film starting position.

* * * * *